United States Patent [19]

Lewis

[11] Patent Number: 5,015,236

[45] Date of Patent: May 14, 1991

[54] INTERMITTENT PATIENT SUCTION SYSTEM, SELF-CONTAINED CONTROL DEVICE THEREFOR AND METHODS OF MAKING THE SAME

[75] Inventor: Jay L. Lewis, Knoxville, Tenn.

[73] Assignee: Robertshaw Controls Company, Richmond, Va.

[21] Appl. No.: 434,792

[22] Filed: Nov. 13, 1989

Related U.S. Application Data

[63] Continuation-in-part of Ser. No. 296,499, Jan. 1, 1989, abandoned.

[51] Int. Cl.⁵ ............................................. A61M 1/00
[52] U.S. Cl. ..................................... 604/120; 137/102
[58] Field of Search ...................... 604/118, 119, 120; 137/102

[56] References Cited

U.S. PATENT DOCUMENTS

| | | | |
|---|---|---|---|
| 2,280,992 | 4/1942 | Wright et al. | 604/118 X |
| 2,337,347 | 12/1943 | McPherson | 604/118 X |
| 3,659,605 | 5/1972 | Sielaff | 128/276 |
| 4,213,457 | 7/1980 | Lewis | 128/276 |
| 4,462,418 | 7/1984 | Xander | 137/624.14 |
| 4,465,090 | 8/1984 | Morgan et al. | 137/102 |
| 4,735,606 | 4/1988 | Davison | 604/118 X |

Primary Examiner—C. Fred Rosenbaum
Assistant Examiner—Corrine Maglione
Attorney, Agent, or Firm—Candor, Candor & Tassone

[57] ABSTRACT

An intermittent patient suction system, a self-contained control device therefor and methods of making the same are provided, the self-contained control device having a housing that contains two restrictor units therein for respectively controlling the "on" time and "off" time that the control device applies a vacuum and does not apply a vacuum through the output of the control device to the patient.

9 Claims, 3 Drawing Sheets

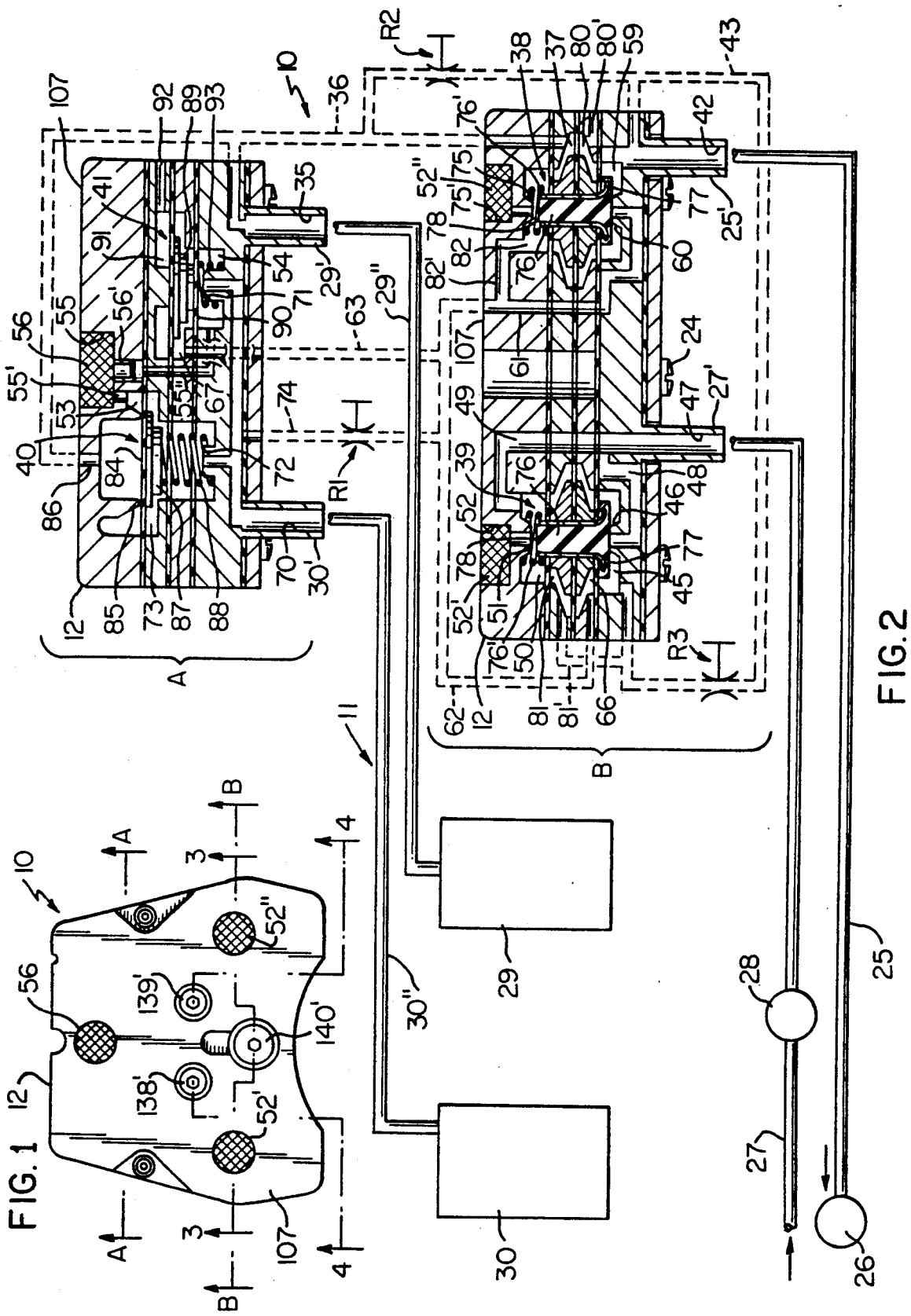

INTERMITTENT PATIENT SUCTION SYSTEM, SELF-CONTAINED CONTROL DEVICE THEREFOR AND METHODS OF MAKING THE SAME

CROSS REFERENCE TO RELATED APPLICATION

This patent application is a Continuation-in-Part patent application of its copending parent patent application, Ser. No. 296,499, filed Jan. 12, 1989, now abandoned.

BACKGROUND OF THE INVENTION

1. Field of the Invention

This invention relates to a new intermittent patient suction system and to a new self-contained control device therefor as well as to new methods for respectively making the new system and the new control device.

2. Prior Art Statement

It is known to provide an intermittent suction system having output means for alternately applying a vacuum and atmospheric pressure to a patient for removing fluids from the patient and wherein the system includes a vacuum source and first and second container means adapted to be interconnected to operating means of a self-contained control device and to the source and the atmospheric pressure by the operating means of the control device that is adapted to apply the vacuum through the output means to the patient in response to a vacuum condition of the first container means and to apply the atmospheric pressure through the output means to the patient in response to a vacuum condition in the second container means, the operating means of the control device having means for always interconnecting the vacuum through the output means to the patient when the vacuum condition in the first container means is a certain percentage of the source regardless of the vacuum value of the source so as to prevent any adverse interruption in the system during the use thereof for the patient should the vacuum level of the source fall to an undesirable level, the control device having a housing means, and two adjustable restrictor means for respectively controlling the "on" time and "off" time that the control device applies the vacuum and does not apply the vacuum through the output means to the patient. For example, see the Lewis U.S. Pat. No. 4,213,457.

It was suggested by another that perhaps the self-contained control device as set forth in the aforementioned Lewis U.S. Pat. No. 4,213,457, could be modified so that such restrictor means thereof, as well as a third restrictor means that controls the flow through the output means, could be disposed in the housing means of the control device so as to be carried thereby. However, such suggestion did not provide any information as to how the physical structure of the restrictor means could be incorporated into a self-contained control device nor how the flow passages of such system within the control device should be modified to accommodate such restrictor means.

Accordingly, applicant then invented the unique arrangement as set forth in FIGS. 1-4.

Subsequent to such arrangement of FIGS. 1-4 having been invented by applicant, it was again suggested by another that perhaps the adjustable restriction means R1 and R2 thereof could be fixed restriction means rather than adjustable restriction means. However, again such suggestion did not provide any information as to how the physical structure of the adjustable restrictor means could be changed nor what new structure should be provided to have fixed restrictor means.

Therefore, applicant then invented the unique arrangement as set forth in FIGS. 5 and 6.

Another intermittent patient suction system is set forth in the Sielaff U.S. Pat. No. 3,659,605.

SUMMARY OF THE INVENTION

One feature of this invention is to provide a new self-contained control device for an intermittent patient suction system wherein the restrictor means for respectively controlling the "on" time and "off" time that the control device applies the vacuum and does not apply the vacuum through the output means of the control device to the patient are disposed within the housing means of the control device to be carried thereby, whereby it is believed that better control of the system may be obtained and that an easier access to the restrictor means will be provided for cleaning of the same.

In addition, it has been found according to the teachings of this invention that each restrictor means permits molded plastic structure to be utilized from the material of the housing means itself and thereby reduce the cost over the cost when the restrictor means are used external to the control device as in the aforementioned prior known system.

Therefore, one embodiment of this invention provides an intermittent suction system having output means for alternately applying a vacuum and atmospheric pressure to a patient for removing fluids from the patient and wherein the system includes a vacuum source and first and second container means adapted to be interconnected to operating means of a self-contained control device and to the source and the atmospheric pressure by the operating means of the control device that is adapted to apply the vacuum through the output means to the patient in response to a vacuum condition of the first container means and to apply the atmospheric pressure through the output means to the patient in response to a vacuum condition in the second container means, the operating means of the control device having means for always interconnecting the vacuum through the output means to the patient when the vacuum condition in the first container means is a certain percentage of the vacuum condition of the source regardless of the vacuum value of the source so as to prevent any adverse interruption in the system during the use thereof for the patient should the vacuum level of the source fall to an undesirable level, the control device having a housing means, and two restrictor means for respectively controlling the "on" time and "off" time that the control device applies the vacuum and does not apply the vacuum through the output means to the patient, the restrictor means being disposed in the housing means of the control device to be carried thereby.

Accordingly, it is an object of this invention to provide a new intermittent patient suction system having one or more of the novel features of this invention as set forth above or hereinafter shown or described.

Another object of this invention is to provide a new method of making such a new intermittent patient suction system, the method of this invention having one or more of the novel features of this invention as set forth above or hereinafter shown or described.

Another object of this invention is to provide a new self-contained control device for such an intermittent patient suction system or the like, the control device of this invention having one or more of the novel features of this invention as set forth above or hereinafter shown or described.

Another object of this invention is to provide a new method of making such a new control device, the method of this invention having one or more of the novel features of this invention as set forth above or hereinafter shown or described.

Other objects, uses and advantages of this invention are apparent from a reading of this description which proceeds with reference to the accompanying drawings forming a part thereof and wherein:

BRIEF DESCRIPTION OF THE DRAWINGS

FIG. 1 is a top view of the new control device of this invention.

FIG. 2 is an enlarged schematic view illustrating the control device of FIG. 1 utilized in the new intermittent patient suction system of this invention, the control device of FIG. 2 comprising sections taken on lines A—A and B—B of FIG. 1 and with such sections being respectively labeled A and B in FIG. 2.

DESCRIPTION OF THE PREFERRED EMBODIMENT

Figure 3:
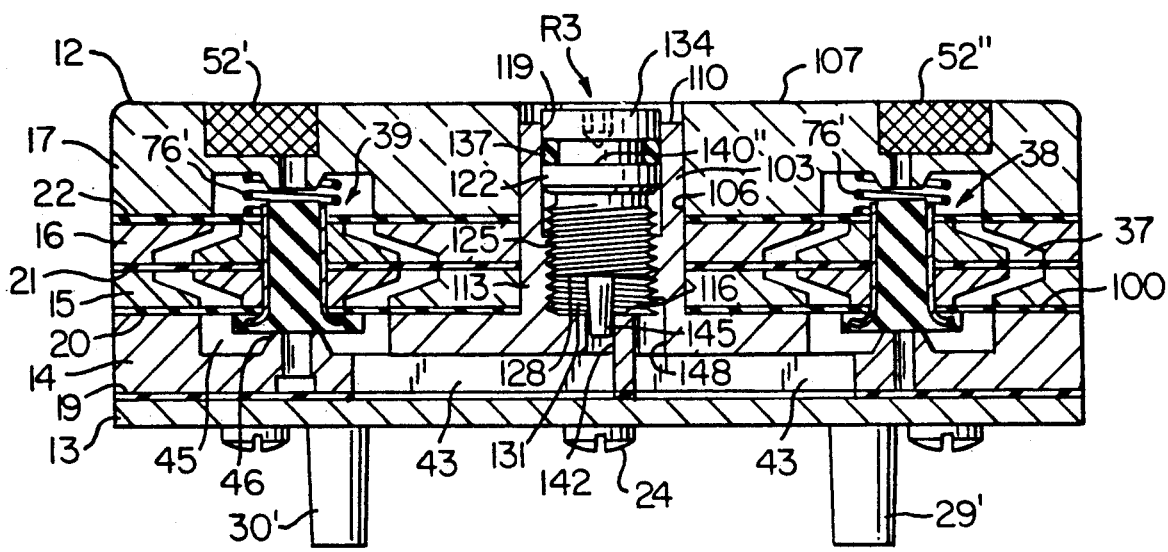
FIG. 3 is an enlarged cross-sectional view of FIG. 1 and is taken on line 3—3 of FIG. 1.

While the various features of this invention are hereinafter described and illustrated as being particularly adapted to provide a self-contained control device for an intermittent patient suction system, it is to be understood that the various features of this invention can be utilized singly or in any combination thereof to provide a control device for other systems as desired.

Therefore, this invention is not to be limited to only the embodiment illustrated in the drawings, because the drawings are merely utilized to illustrate one of the wide variety of uses of this invention.

Referring now to FIGS. 1 and 2, the new control device of this invention is generally indicated by the reference numeral 10 and is utilized for providing a control means for an intermittent patient suction system of this invention that is generally indicated by the reference numeral 11 in FIG. 2.

The control device 10 of this invention is a self-contained unit having a housing means 12 formed from a plurality of plates 13, 14, 15, 16 and 17 suitably stacked together with a plurality of flexible diaphragms 19, 20, 21 and 22 disposed therebetween and all being held together by a plurality of fastening means 24. If desired, the diaphragm 19 can comprise a sealing gasket.

While the housing plates 13–17 can be formed of any suitable material, the same have been formed of plastic material in one working embodiment of this invention wherein the plastic material of the plate 14 is utilized for providing valve seat means or other structure means for restrictor means in a unique manner as hereinafter set forth.

The self-contained unit 10 of this invention readily permits the same to be utilized in already existing control systems for replacing the prior known self-contained unit thereof as well as replacing the external adjustable restriction means thereof, as will be apparent hereinafter, the prior known self-contained unit and intermittent patient suction system that has external restriction means being fully disclosed in the aforementioned Lewis U.S. Pat. No. 4,213,457, whereby this patent is being incorporated into this disclosure by this reference thereto.

Also, the self-contained unit 10 of this invention readily permits the same to be utilized in other already existing control systems by replacing the individual relay units thereof, such as the individual relay units of the aforementioned Sielaff U.S. Pat. No. 3,659,605, whereby this patent is also being incorporated into this disclosure by this reference thereto.

The new intermittent patient suction system 11 of this invention includes a vacuum source conduit 25 for interconnecting to a main vacuum source 26, such as the main vacuum source for a hospital, and a conduit means 27 for interconnecting to a hospital patient for withdrawing fluids therefrom in a manner well known in the art, such as described in the aforementioned U.S. Pat. Nos. 4,213,457 and 3,659,605, the conduit means 27 having a vacuum regulator 28 therein so that the value of the vacuum being applied to a patient through the conduit means 27 will not exceed a safe value thereof.

The system 11 includes a pair of container means 29 and 30, the container means 29 being interconnected to a nipple means 29' of the control device 10 by an external conduit means 29''. Similarly, the container means 30 is interconnected to another nipple means 30' of the control device 10 by an external conduit means 30''.

The external conduit means 25 that leads from the vacuum source 26 is interconnected to a third nipple means 25' of the control device 10 while the external patient conduit means 27 is interconnected to a fourth nipple means 27' of the control device 10.

In this manner, it can be seen that only four nipple means 25', 27', 29' and 30' are provided for the control device 10 of this invention whereas the control device of the aforementioned Lewis U.S. Pat. No. 4,213,457, not only had six nipple means requiring six external conduit means to be respectively interconnected thereto, but also such external conduit means of the prior known control device had external restrictor means therein which have been uniquely incorporated into the self-contained control device 10 of this invention in a manner hereinafter set forth so as to be carried by the housing means 12 thereof. Also, the control device 10 of this invention uses only five plates 13–17 and four diaphragms 19–22 whereas the prior known device of Lewis has six plates and five diaphragms.

While a plurality of passage means are schematically illustrated by dash lines in FIG. 2 as being external to the housing means 12 of the control device 10, it is to be understood that such passage means that are illustrated by dash lines in FIG. 2 are actually formed within the plate means 13–17 and diaphragm means 19–22 of the control device 10 in a manner well known in the art of internally porting and passaging a stacked plate control device so that the actual location of the passage means that are indicated by dash lines in FIG. 2 need not be described in detail in order to understand the features of this invention.

The container means 29 has its interior interconnected by the conduit means 29" to a passage means 35 in the nipple means 29', the nipple passage means 35 interconnecting with an internal passage means 36 in the housing means 12 that leads to a control chamber 37 of a relay unit of the control device 12 that is generally indicated by the reference numeral 38 in FIGS. 2 and 3.

The control unit 10 also includes three other relay units which are respectively and generally indicated by the reference numerals 39, 40 and 41 with each including one or more internal valve seat means adapted to be opened and closed by a movable valve member that is carried by or controlled by a portion of one or more of the flexible diaphragms 20-22 as fully illustrated in the drawings whereby only the details of the relay means 38-41 necessary to fully understand the various features of this invention will be described.

The vacuum source conduit means 25 of the system 11 is interconnected to a passage means 42 in the nipple means 25' and the nipple passage means 42 is, in turn, interconnected by an internal passage means 43 to a chamber 45 of the relay unit 39. The chamber 45 is adapted to be interconnected to a valve seat 46 of the relay unit 39 that leads to an internal passage means 47 of the nipple means 27' by an interconnecting internal passage means 48.

The passage means 47 of the nipple 27' is, thus, interconnected to the patient conduit means 27, the passage 47 of the nipple 27' also being fluidly interconnected to an internal passage means 49 of the control unit 10 that leads to another chamber 50 of the relay unit 39. The chamber 50 is adapted to be interconnected to a valve seat 51 of the relay unit 39 with the valve seat 51 being fluidly interconnected to a vent or atmospheric pressure chamber 52 that supplies atmospheric pressure through a suitable filter 52' to the valve seat 51.

Similarly, a chamber 53 of the relay unit 40 and a chamber 54 of the relay unit 41 are vented by a vent cavity 55 in the housing means 12 having a filter 56 therein and being respectively interconnected to the chambers 53 and 54 by internal passages 55' and 55" for a purpose hereinafter described, the passage 55" having an orifice cup 56' therein to provide a fixed restriction means between the atmosphere and the chamber 54 for a purpose hereinafter described.

The internal passage means 42 of the nipple 25' that is interconnected to the vacuum source 26 by the conduit 25 not only is interconnected to the previously described internal passage 43, but also the same is interconnected to a control chamber 59 of the relay unit 38. The chamber 59 is adapted to be interconnected to a valve seat 60 which is interconnected through internal passage means 61 and 62 to a control chamber 66 of the relay unit 39 and by an internal passage means 63 to a control chamber 67 of the relay unit 41 for a purpose hereinafter described.

The interior of the container means 30 is interconnected by the conduit 30" to an internal passage means 70 of the nipple means 30' that leads not only to a valve seat 71 of the relay unit 41, but also to a nipple 72 of the relay unit 40. The nipple 72 of the relay unit 40 is always open and thereby is continuously interconnected to a control chamber 73 of the relay unit 40 for a purpose hereinafter described.

The passage 70 in the nipple 30' is also fluidly interconnected by an internal passage means 74 to the internal passage means 62 previously described.

The relay unit 38 has a valve seat 75 that leads to a vent cavity or chamber 75' that has a filter 52" therein in a manner similar to the vent chamber 52 for the relay unit 39.

The relay units 38 and 39 of the control unit 10 of this invention each includes a like resilient valve member 76 being carried by portions of the three flexible diaphragms 20, 21 and 22 whereby the ends 77 of the resilient valve members 76 are adapted to respectively open and close the valve seats 60 and 46 while the other ends 78 thereof are adapted to respectively open and close the valve seats 75 and 51 for a purpose hereinafter described.

The relay units 38 and 39 of the control unit 10 have compression springs 76' respectively acting on the members 76 thereof in directions to tend to normally maintain the valve seats 60 and 46 thereof in closed conditions thereof and the valve seats 75 and 51 in the open conditions thereof as illustrated in FIG. 2.

A control chamber 80 of the relay unit 38 that is opposite to the control chamber 37 thereof is interconnected to the atmosphere by a vent passage 80' in the housing plate 15.

A control chamber 81 of the relay unit 39 that is opposite to the control chamber 66 is interconnected to the control chamber 45 by an internal branch passage means 81' as illustrated in FIG. 2.

A chamber 82 of the relay unit 38 is adapted to be interconnected to the valve seat 75 and is also interconnected by an internal passage 82' to the previously described internal passage means 62.

A portion of the diaphragm 22 for the relay unit 40 acts as a valve member 84 for opening and closing a valve seat 85 of the relay unit 40 which projects into the chamber 53 thereof and is interconnected by an internal passage means 86 to the internal passage means 36 of the control unit 10. A rigid backup member 87 is provided for the valve member 84 of the relay unit 40 with the valve member 84 normally being urged to the closed position thereof against the valve seat 85 by a compression spring 88 disposed in the chamber 73 thereof and bearing against the backup member 87.

A spacing member 89 is disposed between portions of the diaphragms 20 and 21 of the relay unit 41 as illustrated in FIG. 2 whereby a portion of the diaphragm 20 forms a valve member 90 for opening and closing the valve seat 71, the spacer 89 being disposed in the chamber 67 of the relay unit 41. A portion of the diaphragm 21 forms a chamber 91 of the relay unit 41 opposite from the chamber 67 thereof, the chamber 91 being interconnected to the atmosphere by a passage 92 as illustrated in FIG. 2.

A small compression spring 93 is disposed in the chamber 54 of the relay unit 41 to tend to move the valve member 90 away from the valve seat 71 as illustrated in FIG. 2.

Figure 4:
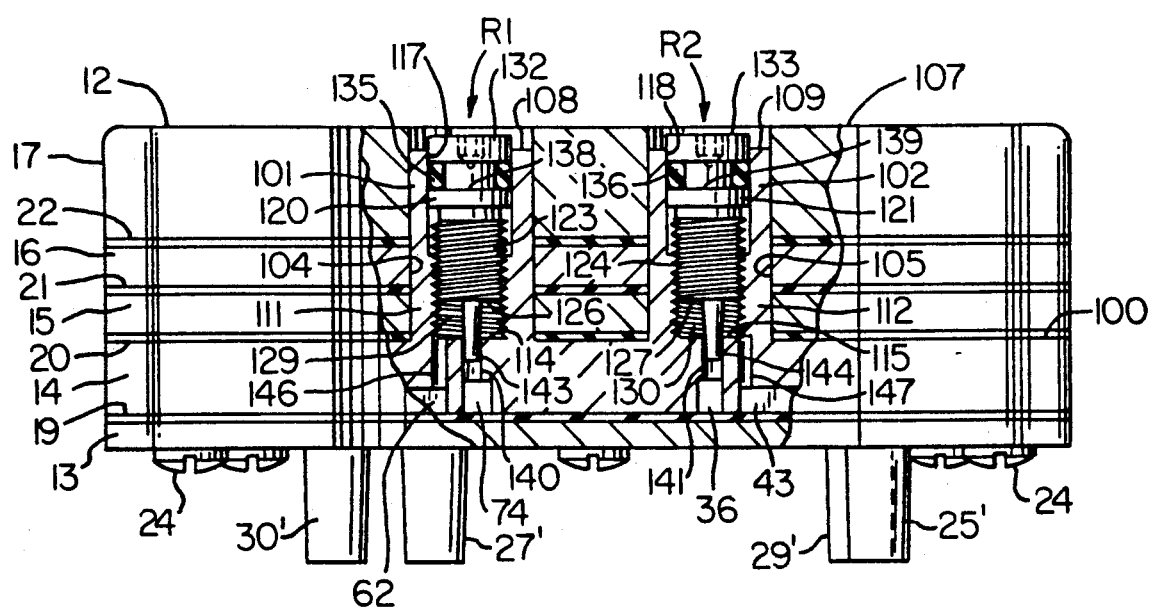
FIG. 4 is an enlarged cross-sectional view of the control device of FIG. 1 and is taken on the line 4—4 of FIG. 1.

The control unit 10 of this invention has three adjustable restrictor means disposed in the housing means 12 thereof with such restrictor means being generally and respectively indicated by the reference designations R1, R2 and R3 in FIG. 2, the restrictor means R3 being illustrated in detail in FIG. 3 and the restrictor means R1 and R2 being illustrated in detail in FIG. 4.

The restrictor means R2 controls the amount of "on" time that the vacuum source 26 is applied to the patient and the restrictor means R1 controls the amount of "off" time that the vacuum source is not applied to the patient on each cycle of operation of the control device 10, the control device 10 when operating applying the vacuum through the output means 27' to the patient and then applying atmospheric pressure through the output means 27' to the patient in a repeating cycle as will be hereinafter set forth. The restrictor means R1 is disposed in the internal passage means 74 and the restrictor means R2 is disposed in the internal passage means 43.

The restrictor means R3 controls the amount of vacuum that goes directly to the patient when the supply vacuum is turned on and is disposed in the passage means 43 at a point intermediate the nipple means 42 and the control chamber 45 of the relay unit 39.

As illustrated in FIGS. 3 and 4, the housing plate 14 has an upper surface 100 and has three integral tubular extensions 101, 102 and 103 extending upwardly therefrom and disposed through suitable openings 104, 105 and 106 formed respectively through the upper housing plates 15, 16, 17 and 18 as well as through the diaphragms 20, 21 and 22 so that the openings 104, 105 and 106 not only receive the tubular members 101, 102 and 103 therein as illustrated in FIGS. 3 and 4 but also the openings 104, 105 and 106 respectively interrupt an outer flat exterior surface means 107 of the housing means 12 as illustrated in FIG. 1 to provide access means to the restrictor means R1, R2 and R3.

The tubular members 101, 102 and 103 of the housing plate 14 respectively have three open ends 108, 109 and 110 which are disposed short of the top surface 107 of the housing means 12 for a purpose hereinafter described.

The tubular members 101, 102 and 103 of the housing plate 14 respectively have the lower portions 111, 112 and 113 thereof internally threaded and terminate respectively at end wall means 114, 115 and 116 of the housing plate 14. The tubular extensions 101, 102 and 103 of the housing plate 14 have the upper internal portions 117, 118 and 119 thereof substantially smooth and respectively defining substantially circular transverse cross-sectional configurations throughout the length thereof to the open ends 108, 109 and 110 thereof.

The restrictor means R1, R2 and R3 respectively comprise threaded adjusting parts or members 120, 121 and 122 respectively having externally threaded portions 123, 124 and 125 threaded in the respective threaded portions 111, 112 and 113 of the tubular members 101, 102 and 103 and having end walls 126, 127 and 128 thereof respectively cooperating with the end walls 114, 115 and 116 of the housing plate 14 to define cavities 129, 130 and 131 therebetween.

Upper cylindrical portions 132, 133 and 134 of the adjustable members 120, 121 and 122 respectively carry annular sealing O-rings 135, 136 and 137 in annular grooves 138, 139 and 140" thereof to respectively seal against the internal peripheral surfaces of the tubular portions 101, 102 and 103 throughout the axial adjusting positions of the adjustable members 120, 121 and 122.

Exposed ends 138', 139' and 140' of the respective adjustable members 120, 121 and 122 have suitable slots or central depressions formed therein to facilitate the rotation of the adjusting members 120, 121 and 122 with a suitable turning tool for threading the same to the desired positions within the tubular members 101, 102 and 103. Thus, it can be seen that the adjustable members 120–123 are readily accessible at the top or flat end surface means 107 of the self-contained control device 10 of this invention.

The housing plate 14 has a plurality of cylindrical openings 140, 141 and 142 formed therethrough and respectively leading from the passage means 74, 43 and 43 to the respective cavities 129, 130 and 131 formed by the adjustable members 120, 121 and 122 of the restrictor means R1, R2 and R3 and the respective tubular portions 101, 102 and 103 of the housing plate 14, the openings 129, 130 and 131 respectively receiving centrally depending conical flow controlling projections or throttling portions 143, 144 and 145 of the adjusting members 120, 121 and 122 therein. In this manner, the openings 140, 141 and 142 respectively define valve seats that have the amount of flow therethrough being controlled by the axial position of the respective projections 143, 144 and 145 of the adjusting members 120, 121 and 122 therein in a manner well known in the art for adjustable restrictor means or for adjustable orifice means.

The cavities 129, 130 and 131 of the respective restrictor means R1, R2 and R3 are also respectively interconnected to the other parts of the internal passage means 62, 43 and 36 by non-controlled opening means 146, 147 and 148 whereby the restrictor means R1 controls the flow through the internal passage means 74 at the location illustrated in FIG. 2, the restrictor means R2 controls the flow through the internal passage means 36 at the location illustrated in FIG. 2 and the restrictor means R3 controls the flow through the internal passage means 81' at the location illustrated in FIG. 2.

In this manner, it can be seen that the restrictor means R1, R2 and R3 are adapted to be respectively adjustable at the surface means 107 of the housing means 12 of the self-contained control unit 10 of this invention so as to permit a person to set the amount of "on" time that the vacuum source is to be applied to the patient and the amount of "off" time that the vacuum is not to be applied to the patient and the atmosphere pressure is to be applied to the patient in each cycle and to set the restrictor means R3 to control the amount of vacuum that is to be applied during that "on" time as will be apparent hereinafter, the setting of the restrictors R1, R2 and R3 taking place by simple rotational adjustments of the respective adjusting members 120, 121 and 122. Also, it can be seen that by forming the housing plate 14 of suitable plastic material, the housing plate 14 can be molded into the desired configuration and have the valve seat means for the adjustable members 120, 121 and 122 thereof formed by molding opening means 140, 141 and 142 therein in a simple manner as previously set forth whereby the cost of providing separate valve seats is eliminated.

In addition, it is believed that by having the restrictor means R1, R2 and R3 as part of the self-contained unit 10, better control can be obtained and easier access is provided for cleaning the restrictor means R1, R2 and R3 and/or for changing the threaded members or parts 120, 121 and 122, as desired.

From the above, it can be seen that the new self-contained control unit 10 of this invention can be formed in a relatively simple manner to provide a single package containing the relay units 38, 39, 40 and 41 as well as the restrictor means R1, R2 and R3 to operate in the new system 11 of this invention in a manner now to be described.

When the system 11 is initially interconnected to the vacuum source 26 by the conduit means 25 and the conduit means 27 is initially interconnected to the patient and while the force of the compression spring 76' in the relay unit 38 tends to hold the valve member 76 closed against the valve seat 60, the vacuum now being created in the chamber 59 of the relay unit 38, in effect, pulls downwardly on the effective portion of the diaphragm 20 to hold the valve member 76 in its closed condition against the valve seat 60. While the force of the compression spring 76' of the relay means 39 tends to hold the valve member 76 thereof against the valve seat 46 as illustrated in FIG. 2, the vacuum now being created in the larger diameter control chamber 81 over the vacuum being created in the chamber 45 overcomes the force of the spring 76' and moves the valve member 76 upwardly to close the valve seat 51 and to open the valve seat 46 so that the vacuum is applied by passage means 43 through open valve seat 46 and interconnecting passages 48 and 47 to the patient conduit 27 to withdraw fluid from the patient, the amount of flow of fluid from the patient being controlled by the setting of the restrictor R3.

At this time, the vacuum source 26 is continuously evacuating the interior of the container means 29 through the passage means 43, 36 and 35 that are interconnected to the conduit means 29", the time of evacuating the container means 29 having been set by setting the restrictor means R2. This reduction of the pressure in the container means 29 also causes, by means of the passage means 36 of the control unit 10, an evacuation of the control chamber 37 of the relay unit 38.

The force of the spring 76' of the relay unit 38 and the sizes of the effective portions of the diaphragms 20 and 21 of the relay unit 38 have been so selected that the valve member 76 thereof will remain closed against the valve seat 60 until the vacuum value in the chamber 37 reaches a certain percentage of the vacuum value in the chamber 59, regardless of the vacuum value of the main vacuum source 26.

In the embodiment of the control system 11 illustrated in the drawings, the relay unit 38 has been so constructed and arranged that when the vacuum value being created in the container means 29 and, thus, in the control chamber 37 of the relay unit 38 reaches approximately 50 percent of the vacuum value of the vacuum source 26 and, thus, the vacuum value in the chamber 59 of the relay unit 38, the valve member 76 of the relay unit 38 is switched from the condition illustrated in FIG. 2 to move upwardly and open the valve seat 60 while closing the valve seat 75.

Thus, when a vacuum signal of approximately 50 percent of the supply vacuum signal acts on the large diaphragm 21 of the relay unit 38, the poppet or valve member 76 thereof is effectively unbiased and will permit some vacuum to act through the valve seat 60 and by means of the internal passage 61 being interconnected to the chamber 82, this creates a supply vacuum to the top of the third diaphragm 22 attached to the valve member 76 and supplements the bias provided by the vacuum in the on volume container 29 acting in the chamber 37. The valve member 76 is then unbalanced and will switch with a snap action. The "on" restrictor R2 and the "on" vacuum cavity of the container 29 is supplied with supply vacuum continuously and by adjusting the restrictor means R2, the amount of "on" time can be regulated before the valve member 76 of the relay unit 38 is switched in the above manner.

When the relay 38 transfers, the valve member 76 of the relay unit 38 closes the valve seat 75 and thereby disconnects the atmosphere at the vent chamber 75' from the control chamber 66 of the relay unit 39 while, in effect, interconnecting the vacuum source 26 to the control chamber 66 of the relay unit 39 by means of the now open valve seat 60 and interconnecting passage means 61 and 62 whereby the valve member 76 of the relay unit 39 is moved downwardly by the vacuum now being created in the control chamber 66 that adds to the vacuum in the chamber 45 and the force of the spring 76' to overcome the vacuum in the chamber 81.

The downward movement of the valve member 76 of the relay unit 39 causes the valve member 76 to close the valve seat 46 and open the valve seat 51 whereby the chamber 50 is now interconnected to the atmosphere which is applied to the patient conduit 27 by the interconnecting passage means 49, 47 and patient conduit 27 as long as the valve member 76 of the relay unit 30 is in its down condition.

At this time, the patient conduit 27 is now interconnected to atmospheric pressure by the opened valve seat 51 of the relay unit 39 so that withdrawn patient fluid in the patient conduit 27 now can partially flow backwardly to the patient for the reasons fully set forth in the aforementioned U.S. Pat. Nos. 4,213,457 and 3,659,605 for a period of "off" time until the vacuum value in the container means 30 reaches a certain value as will be apparent hereinafter.

In particular, the opening of the valve seat 60 of the relay unit 38 to interconnect the vacuum source conduit means 25 to the internal passage means 61 also interconnects the vacuum source conduit means 25 to the interior of the container means 30 through the restrictor means R1 and passage means 74 and nipple means 30' whereby the interior of the container means 30 begins to evacuate because the valve seat 71 of the relay unit 41 has now been closed by its valve member 90 as the branch interior passage means 63 has now evacuated the control chamber 67 so as to pull downwardly on the diaphragm 21 of the relay unit 41 in opposition to the force of the compression spring 93. This disconnects the vent chamber 55 from the interior of the container means 30.

In particular, when the control chamber 66 of the relay unit 39 is evacuated in the above manner, an evacuation of the control chamber 67 of the relay unit 41 also takes place by means of the interconnecting passage means 63 whereby the resulting pressure differential across the larger effective portion of the diaphragm 21 of the relay unit 41 causes the valve member 90 to move downwardly in FIG. 2 and close the valve seat 71 in opposition to the force of the spring 93.

As the container means 30 is being evacuated in the above manner, such evacuation of the interior of the container means 30 is also being sensed in the chamber 73 of the relay unit 40 by means of the conduit means 30", nipple 30', passage 70 and nipple 72 of the relay unit 40 whereby the evacuation of the chamber 73, in effect, tends to act on the effective portion of the diaphragm 22 of the relay unit 40 to pull the valve member 84 downwardly not only in opposition to the force of the compression spring 88, but also in opposition to the force of the vacuum in the valve seat 85 which is the same vacuum value as the vacuum created in the container means 29 because the interior of the container means 29 is interconnected to the valve seat 85 by means of the conduit 29", nipple 29', passage 35 and passage 36.

Accordingly, when the vacuum value in the container means 30 reaches a certain percentage of the vacuum value in the container means 29, which in the embodiment of the control system 11 illustrated in FIG. 2, is approximately 50 percent, the valve member 84 of the relay unit 40 is moved downwardly to open the valve seat 85 and thereby interconnect not only the interior of the container means 29 to atmospheric pressure by means of the vent chamber 55, passage 53, open seat 85, passage 36, passage 35, nipple 29' and conduit means 29", but also to interconnect the control chamber 37 of the relay unit 38 to atmospheric pressure by the passage means 53 through the passage means 36.

Thus, the dumping of the vacuum in the control chamber 37 of the relay unit 38 causes the valve member 76 thereof to be moved downwardly by the vacuum in the chamber 59 thereof and the force of the spring 76' and thereby close the valve seat 60 to not only disconnect the vacuum source conduit 25 from the valve seat 60 and, thus, from the control chamber 66 of the relay unit 39, but also through the opening of the valve seat 75 to dump the vacuum in the control chamber 66 of the relay unit 39 to atmosphere through the now open valve seat 75 whereby the valve member 76 of the relay unit 39 again moves upwardly in opposition to the force of the spring 76' thereof by the vacuum in the control chamber 81 to open the valve seat 45 and close the valve seat 51 and thereby again interconnect the vacuum source conduit 25 through the valve seat 46 to the patient conduit 27. The dumping of the vacuum in the control chamber 66 of the relay unit 39 also dumps the vacuum in the control chamber 67 of the relay unit 41 whereby the valve member 90 of the relay unit 41 moves upwardly in FIG. 2 to open the valve seat 71 and thereby again interconnect the vent chamber 54 of the relay unit 41 to the interior of the container means 30 to dump the vacuum therein to the atmosphere at a rate controlled by the fixed restrictor means 56'. The opening of the valve seat 71 of the relay unit 41 also now dumps the vacuum in the chamber 73 of the relay unit 40 to thereby cause the valve member 84 to move against the valve seat 85 to disconnect the interior of the container means 29 from the vent chamber 53 of the relay unit 40.

At this time the patient conduit 27 is now interconnected to the vacuum source 26 by the opened valve seat 46 of the relay unit 39 so that fluid can be withdrawn from the patient.

From the above, it can be seen that the system 11 and the control unit 10 of this invention will intermittently interconnect the vacuum source 26 to the patient conduit 27 for a certain "on" time period as set by the restrictor means R2 and then disconnect the vacuum source 26 from the patient conduit 27 while interconnecting the atmospheric pressure thereto for a certain "off" time period as determined by the restrictor means R1 in a continuous cycling manner as long as the control system 11 is interconnected to the vacuum source 26 through the conduit means 25, the volume size of the container means 29 and 30 and the adjustment of the restrictor means R2 and R1 can be such that the vacuum source 26 is interconnected to the patient conduit means 27 for approximately 15 seconds while the atmospheric pressure is interconnected to the patient conduit means 27 for approximately 7½ seconds. However, any time period adjustments can be made with the restrictor means R1 and R2 as previously set forth.

From the above, it can be seen that the control system 11 and control means 10 of this invention therefore will provide the aforementioned cycling operation of interconnecting the vacuum source 26 to the patient conduit means 27 for a certain "on" time period as determined by the setting of the restrictor means R2 and then interconnect the atmospheric pressure to the patient conduit means 27 for a certain ""off" time period as determined by the setting of the restrictor means R1 regardless of the vacuum value of the vacuum source 26 because such switching operation is merely based on the vacuum value in the container means 29 being a certain percentage of the vacuum value of the main vacuum source 26 and not on a specific value thereof.

In addition, the changing from the interconnection of the vacuum source 26 to the patient conduit 27 to the interconnection of the atmospheric pressure to the patient conduit 27 is also merely dependent upon the vacuum value of the container means 30 becoming a certain percentage of the vacuum value of the vacuum supply 26 or the vacuum value in the container means 29 whereby the control system 11 of this invention will operate within a vacuum value of the main vacuum source 26 so that the system 11 will function whether the vacuum value of the main source 26 of the hospital is high or low or continuously varying as fully set forth in the aforementioned Lewis U.S. Pat. No. 4,213,457.

Thus, it can be seen that the intermittent suction system 11 of this invention has output means 27' for alternately applying a vacuum and atmospheric pressure to a patient for removing fluids from the patient and wherein the system includes a vacuum source 26 and first and second container means 30 and 29 adapted to be interconnected to operating means 38-41 of a self-contained control device 10 and to the source 26 and the atmospheric pressure by the operating means 38-41 of the control device 10 that is adapted to apply the vacuum through the output means 27' to the patient in response to a vacuum condition of the first container means 30 and to apply the atmospheric pressure through the output means 27' to the patient in response to a vacuum condition in the second container means 29, the operating means 38-41 of the control device 10 having means for always interconnecting the vacuum through the output means 27' to the patient when the vacuum condition in the first container means 30 is a certain percentage of the vacuum condition of the source 26 regardless of the vacuum value of the source 26 so as to prevent any adverse interruption in the system 11 during the use thereof for the patient should the vacuum level of the source 26 fall to an undesirable level, the control device 10 having a housing means 12, and two adjustable restrictor means R2 and R1 for respectively controlling the "on" time and "off" time that the control device applies the vacuum and does not apply the vacuum through the output means 27' to the patient, the adjustable restrictor means R1 and R2 being disposed in the housing means 12 of the control device 10 to be carried thereby.

From the above, it can be seen that once the restrictor means R1 and R2 have been set in particular positions thereof, such as to provide the aforementioned arrangement wherein the vacuum source 26 is interconnected to the patient conduit means 27 for approximately 15 seconds and then the atmospheric pressure is interconnected to the patient conduit means 27 for approximately 7½ seconds, such restrictor means R1 and R2 need not thereafter be adjusted as long as such a timing arrangement is desired.

Therefore, in effect, the restrictor means R1 and R2, once set for a particular arrangement, become fixed resistor means so that should it be desired to have the system only provide such a particular timed relationship as previously set forth, then the restrictor means R1 and R2 could be so constructed and arranged that the same are fixed resistor means so as to prevent someone from changing the timed relationship thereof in the field. However, even with fixed resistor means, it was found that it was desirable that such fixed resistor means be made changeable in the field so that the timing relationship provided by the control unit could be changed in the field.

Figure 6:
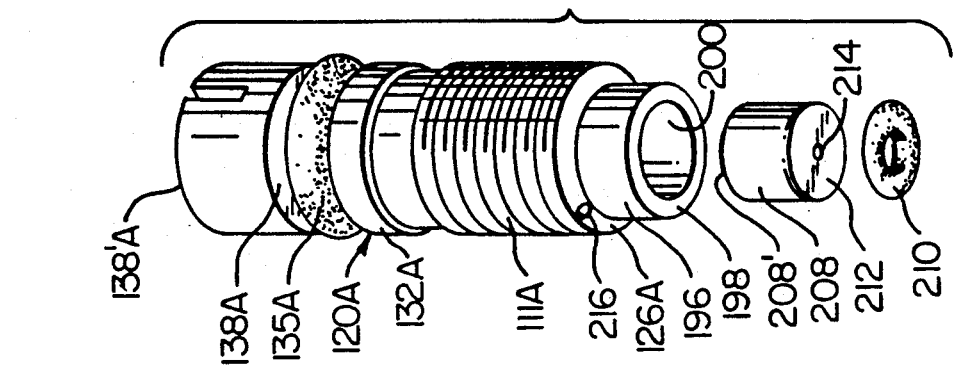
FIG. 6 is an exploded perspective view of one of the changeable restriction means of the control device of FIG. 5.
Figure 5:
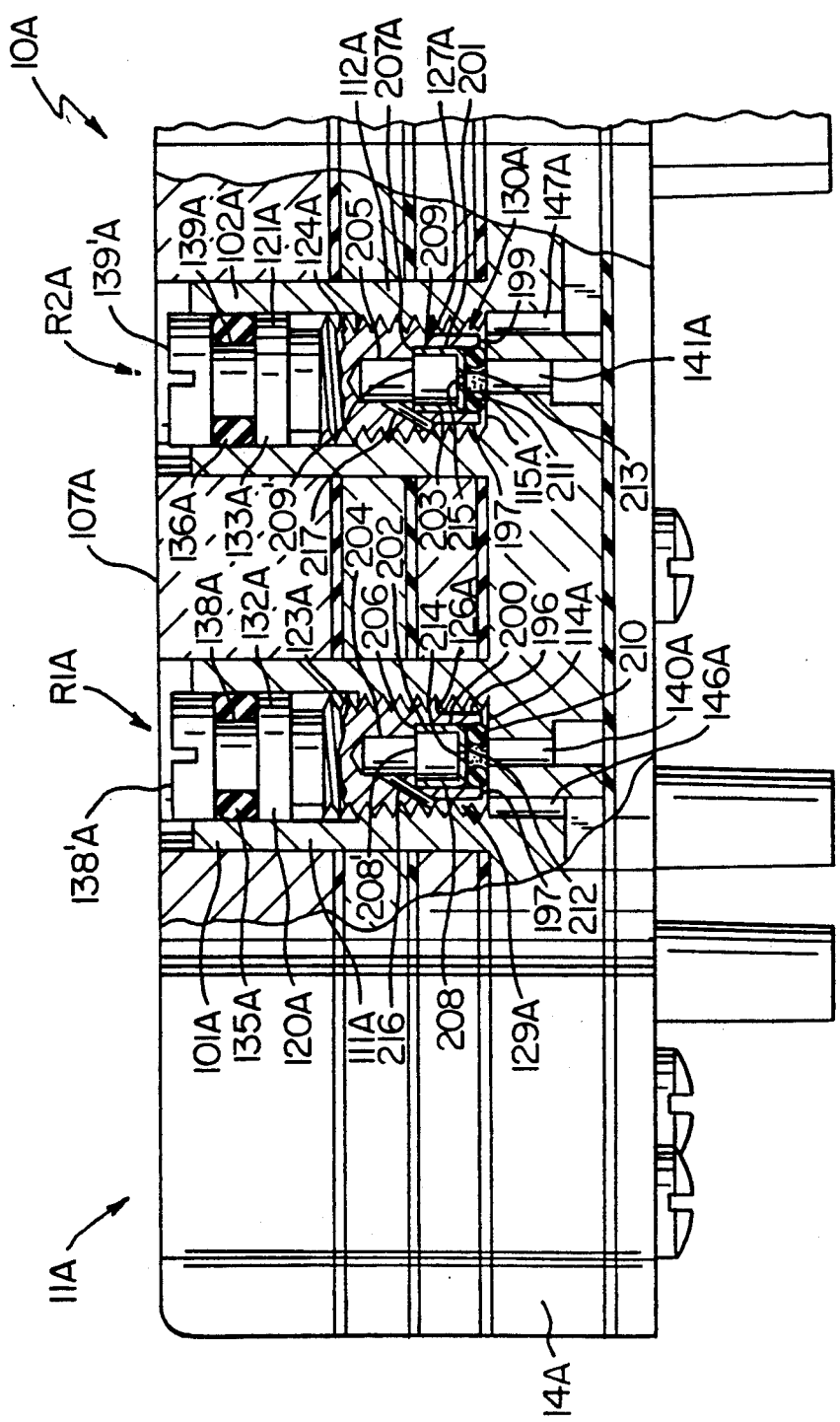
FIG. 5 is an enlarged view similar to FIG. 4 and illustrates another control device of this invention.

Therefore, such an arrangement is provided by this invention and is illustrated in FIGS. 5 and 6 wherein parts thereof that are similar to the parts of the system 11 and the control unit 10 previously described are indicated by like reference numerals followed by the reference letter "A".

As illustrated in FIG. 5, the control unit 10A of this invention is substantially the same as the control unit 10 previously described except that the restrictor means R1A and R2A thereof are fixed restrictor means rather than adjustable restrictor means and the same operate in the control unit 10A to provide a control system 11A that is substantially identical to the control system 11 previously set forth except that a person cannot adjust the timing relation provided by the restrictor means R1A and R2A unless the same are removed from the control unit 10A and new fixed restrictor means R1A and R2A are replaced in the control unit 10A as will be apparent hereinafter.

The restrictor means R1A and R2A respectively comprise threaded parts or members 120A and 121A respectively having threaded portions 123A and 124A threaded in the respective threaded portions 111A and 112A of the tubular members 101A and 102A of the housing plate 14A and having end walls 126A and 127A thereof respectively cooperating with the end walls 114A and 115A of the housing plate 14A to define the cavities 129A and 130A therebetween. The upper cylindrical portions 132A and 133A of the parts or members 120A and 121A respectively carry the annular sealing O-rings 135A and 136A in the annular grooves 138A and 139A thereof to respectively seal against the internal peripheral surfaces of the tubular portions 101A and 102A throughout. Exposed ends 138'A and 139'A of the respective parts or members 120A and 121A have suitable slots or central depressions formed therein to facilitate the rotation of the parts or members 120A and 121A with a suitable turning tool for threading the same to the final positions thereof within the tubular members 101A and 102A or for removing the parts or members 120A and 121A from the tubular members 101A and 102A whereby it can be seen that the members 120A and 121A are readily accessible at the top or flat end surface means 107A of the self-contained control device 10A of this invention and therefore are changeable in the same manner as the threaded adjusting parts or members 120 and 121 previously described.

However, the threaded parts or members 120A and 121A do not have the throttling portions 143 and 144 of the adjusting members 120 and 121 extending from the end walls 126A and 127A thereof but instead have reduced cylindrical portions 196 and 197 extending from the end walls 126A and 127A thereof and terminating in end walls 198 and 199 that are interrupted by stepped openings 200 and 201 that define internal cylindrical sections 202 and 203 respectively separated from smaller cylindrical sections 204 and 205 by annular shoulders 206 and 207.

Orifice cups 208 and 209 formed of any suitable material, such as metallic material, are respectively disposed in the larger cylindrical sections 202 and 203 and have the open ends 208' and 209' thereof respectively disposed against the shoulders 206 and 207 as illustrated. Thereafter, suitable flexible O-rings 210 and 211 are respectively disposed in the openings 200 and 201 to bear against the closed end walls 212 and 213 of the orifice cups 208 and 209 as well as to extend out of the openings 200 and 201 beyond the end walls 126A and 127A thereof for respectively sealing against the flat surfaces 114A and 115A of the housing plate 14A and the closed end walls 212 and 213 of the orifice cups 208 and 209 to thereby communicate the openings 140A and 141A in the end housing plate 14A to the respective orifices 214 and 215 in the end walls 212 and 213 and thus to the smaller cylindrical sections 204 and 205 of the parts 120A and 121A as illustrated.

The threaded members 120A and 121A respectively have angled bores 216 and 217 that interrupt the end walls 126A and 127A thereof outboard of the tubular portions 196 and 197 thereof to respectively place the cavities 129A and 130A in communication with the cylindrical section 204 and 205 thereof and thus in fluid communication with the openings 146A and 144A in the housing plate 14A.

Thus, it can be seen that by threading the threaded members or parts 120A and 121A in the tubular portions 101A and 102A of the housing plate 14A to the final positions thereof as illustrated in FIG. 5 so that the O-rings 210 and 211 respectively seal with the end walls 114A and 115A, the orifices 214 and 215 respectively provide the restriction means R1A and R2A for the control device 10A in the same manner that the adjustable restriction means R1 and R2 provided restriction means for the control device 10 once the restriction means R1 and R2 have been set to the desired setting thereof to provide a desired timed operation.

Therefore, since the control device 10A and system 11A of this invention as set forth in FIG. 5 operate in substantially the same manner as the control device 10 and system 11 previously described in connection with FIGS. 1-4, the operation of the control device 10A and system 11A of this invention need not be further described as it is to be understood that the same operate in the same manner as the control device 10 and system 11 once the adjustable restrictors R1 and R2 thereof have been set in a particular position thereof to provide a desired timed function for having the vacuum source interconnected to the patient for a certain period of time and then the atmosphere interconnected to the patient for another certain period of time in a repeating cycling manner.

However, it can be seen that when it is desired to change the timed relationship provided by the control device 10A of this invention, the threaded parts 120A and 121A can be unthreaded from the tubular members 101A and 102A of the housing plate 14A and either new threaded parts 120A and 121A with their orifice cups 208 and 209 having different sized orifices 214 and 215 to provide a different timed relationship can be reinserted in the tubular members 101A and 102A of the housing plate 14A or merely the orifice cups 208 and 209 of the removed threaded parts 120A and 121A could be readily replaced with new orifice cups 208 and 209 having different sized orifices 214 and 215 therein by merely removing the O-rings 210 and 211 and the original orifice cups 208 and 209 and then replacing new orifice cups 208 and 209 in the threaded parts 120A and 121A together with the O-rings 210 and 211 to provide for new timed relationships for the restrictor means R1A and R2A to be replaced into the control unit 10A in the manner previously set forth.

Of course, it is to be understood that only one of the restrictor means R1A and R2A need be changed to change the timed relationship provided by the control device 10A.

Thus, it can be seen that the control device 10 with its restrictors R1 and R2 and the control device 10A with its restrictors R1A and R2A respectively have changeable restrictors with the restrictors R1 and R2 being changeable by adjusting the position of the frusto-conical throttling portion 143 and 144 thereof to set new size restrictions or to be replaced with new threaded members 120 and 121 with different sized tapering parts thereon whereas the restrictor means R1A and R2A can be changeable by merely changing the orifice cups 208 and 209 thereof after the threaded parts 120A and 121A have been completely removed from the control device 10A in the manner previously set forth.

Therefore, it can be seen that this invention not only provides a new intermittent patient suction system and method of making the same, but also this invention provides a new self-contained control unit or device for such a system and a method of making the same.

While the forms and methods of this invention now preferred have been illustrated and described as required by the Patent Statute, it is to be understood that other forms and method steps can be utilized and still fall within the scope of the appended claims wherein each claim sets forth what is believed to be known in each claim prior to this invention in the portion of each claim that is disposed before the terms "the improvement" and sets forth what is believed to be new in each claim according to this invention in the portion of each claim that is disposed after the terms "the improvement" whereby it is believed that each claim sets forth a novel, useful and unobvious invention within the purview of the Patent Statute.

What is claimed is:

1. In an intermittent suction system having output means for alternately applying a vacuum and atmospheric pressure to a patient for removing fluids from said patient and wherein said system includes a vacuum source and first and second container means adapted to be interconnected to operating means of a self-contained control device and to said source and said atmospheric pressure by said operating means of said control device that is adapted to apply said vacuum through said output means to said patient in response to a vacuum condition of said first container means and to apply said atmospheric pressure through said output means to said patient in response to a vacuum condition in said second container means, said cooperating means of said control device having means for always interconnecting said vacuum through said output means to said patient when said vacuum condition in said first container means is a certain percentage of the vacuum condition of said source regardless of the vacuum value of said source so as to prevent any adverse interruption in said system during the use thereof for said patient should the vacuum level of said source fall to an undesirable level, said control device having a housing means that comprises a plurality of plates disposed in stacked relation so that two of said plates define outer plates and the remainder of said plates define inner plates, and two restrictor means for respectively controlling the "on" time and "off" time that said control device applies said vacuum and does not apply said vacuum through said output means to said patient, the improvement wherein said restrictor means are disposed in said housing means of said control device and are carried solely by one of said inner plates thereof.

2. A system as set forth in claim 1 wherein said restrictor means are disposed in side-by-side relation in said housing means of said control device.

3. A system as set forth in claim 1 and including a third restrictor means that controls the flow through said output means, said third restrictor means being disposed in said housing means of said control device and is carried solely by said one of said inner plates thereof.

4. A system as set forth in claim 1 wherein said one of said inner plates has two openings formed therethrough and defining part of said restrictor means.

5. A system as set forth in claim 4 wherein one of said outer plates of said housing means has a substantially flat exterior surface means, said restrictor means being changeable at said exterior surface means of said housing means.

6. A system as set forth in claim 4 wherein each said restrictor means has a part thereof that is threadedly disposed in its respective opening of said one of said inner plates.

7. A system as set forth in claim 6 wherein each said part of each said restrictor means has a throttling portion that adjusts the size of its respective restrictor means when that said part is rotated in its said opening within certain limits thereof.

8. A system as set forth in claim 6 wherein each said part of each said restrictor means has an orifice cup that cooperates with said one of said inner plates to define that said restriction means when that said part is in a certain threaded relation with said one of said inner plates.

9. A system as set forth in claim 8 wherein each said part of each said restrictor means has a free end means provided with a cavity interrupting the same, said orifice cup of each said restrictor means being replaceable disposed in said cavity of its respective part so as to be carried thereby.

* * * * *

UNITED STATES PATENT AND TRADEMARK OFFICE
CERTIFICATE OF CORRECTION

PATENT NO.   :   5,015,236
DATED        :   May 14, 1991
INVENTOR(S)  :   Jay L. Lewis It is certified that error appears in the above—identified patent and that said Letters Patent is hereby corrected as shown below:

Column 16, line 2, cancel "cooperating" and insert --operating--.

Signed and Sealed this

Twentieth Day of September, 1994

Attest:

BRUCE LEHMAN

Attesting Officer        Commissioner of Patents and Trademarks